United States Patent [19]

Okada et al.

[11] Patent Number: 5,250,705
[45] Date of Patent: Oct. 5, 1993

[54] OPTICALLY ACTIVE CYCLIC AMINE AND THE PROCESS OF OPTICAL RESOLUTION THEREFOR

[75] Inventors: Tetsuo Okada; Tadahiko Tsushima, both of Osaka, Japan

[73] Assignee: Shionogi & Co., Ltd., Osaka, Japan

[21] Appl. No.: 955,246

[22] Filed: Oct. 1, 1992

Related U.S. Application Data

[62] Division of Ser. No. 789,079, Nov. 7, 1991, abandoned.

[30] Foreign Application Priority Data

Nov. 21, 1990 [JP] Japan .................. 2-319107

[51] Int. Cl.$^5$ .................. C07D 207/04; C07D 207/22
[52] U.S. Cl. .................................. 548/557
[58] Field of Search ........................ 548/557

[56] References Cited

U.S. PATENT DOCUMENTS 5,017,581  3/1991  Nishitani et al. ............ 514/312

*Primary Examiner*—Mary C. Lee
*Assistant Examiner*—Joseph K. McKane
*Attorney, Agent, or Firm*—Wenderoth, Lind & Ponack

[57] ABSTRACT

The present invention relates to process for the isolation of (−)-(S)-3-methylamino-4-methylenepyrrolidine derivatives of the formula:

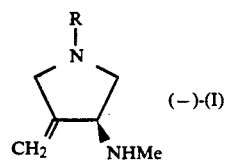

wherein R is hydrogen or amino-protecting group, from the racemic mixture of them comprising the salt formation of the racemate with L-(+)-tartaric acid in a molar ratio of 2:1 and subsequent treatment with a base, and optionally followed by deprotection of the amino-protecting group.

By this process, complicated procedure in resolutional crystallization is not necessary and (−)-(S)-3-methylamino-4-methylenepyrrolidine derivatives can be obtained as optically pure form in above 90% yield quantitatively by single procedure.

1 Claim, No Drawings

OPTICALLY ACTIVE CYCLIC AMINE AND THE PROCESS OF OPTICAL RESOLUTION THEREFOR

This application is a division of now abandoned application Ser. No. 07/789,079 filed on Nov. 7, 1991, now abandoned.

BACKGROUND OF THE INVENTION

1. Field of the Invention

This invention relates to simple but efficient process for optical resolution of 3-methylamino-4-methylenepyrrolidine derivatives of the formula (I):

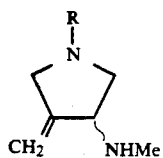

wherein R is hydrogen or amino-protecting group,

2. Prior Art

The racemic compound (I) mentioned above is known as key material for a certain substituent to be introduced into various pyridonecarboxylic acid-type antibacterials including quinoline-type, naphthyridine-type, pyridopyrimidine-type, and cinnoline-type ones.

For example, pyridonecarboxylic acid type antibacterials possessing 3-methylamino-4-methylenepyrrolidin-1-yl as substituent are disclosed in U.S. Pat. No. 5,017,581. Further, it is confirmed from the recent study by the present inventors that among such quinolone type antibacterials, their (−)-form ones have excellent antibacterial activities with less side-effect. But the optical resolution of the final product is uneconomical because of useless process. Therefore, asymmetric synthesis or optical resolution of this substituent is quite desirable. But asymmetric syntheses usually require long processes and are not practically uneconomic. When known method of optical resolution (Optical Resolution Procedures for Chemical Compounds ed. Paul Newman 1981) is adopted to the compound (I), it is difficult to obtain the pure compound with ease, large quantity, and low-priced because of the low resulution ability, optical impurity, complicated reaction, and unusual and expensive reagent. In case of adapting tartaric acid, usually, a molar ratio of amino compound and tartaric acid is 1:1. But when this method is adapted to the compound (I), the yield is low and the recrystallization is required for several times.

SUMMARY OF THE INVENTION

The present invention provides the processes to obtain optically pure (−)-3-methylamino-4-methylenepyrrolidine derivatives with simplicity but in high yield. Furthermore, this process is characterized by the salt formation of pyrroridine derivative with L-(+)-tartaric acid in a molar ratio of 2:1.

DETAILED DESCRIPTION

The present inventors have devoted themselves to study on solving these problems. As a result, they found that the compound of the formula (I):

wherein R has the same meaning as defined above, easily gives crystals as its optically pure salt with L-(+)-tartaric acid by the treatment with L-(+)-tartaric acid in a molar ratio of 2:1. This invention is based on those findings above.

L-(+)-tartaric acid used in this invention is very cheap and the resolution can be conducted in the half amount of usual use. And in this case, complicated procedure in resolutional crystallization is not necessary and (−)-(S)-3-methylamino-4-methylenepyrrolidine derivatives can be obtained as optically pure form in above 90% yield quantitatively by single procedure.

In other words, this invention provides processes for the isolation of the compound of the formula:

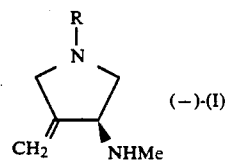

wherein R has the same meaning as defined above, which comprises (a) salt formation of the compound (I) of the formula:

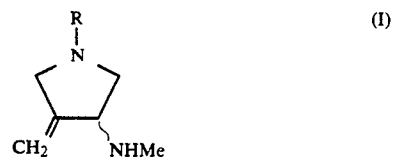

wherein R has the same meaning as defined above, with L-(+)-tartaric acid in a molar ratio of 2:1 to give the compound (II) of the formula:

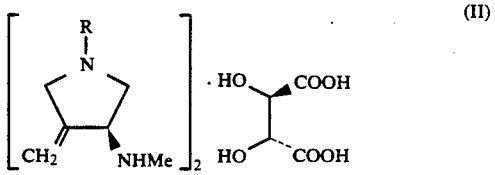

and (b) subsequent treatment of said tartarate (II) with a base such as sodium hydroxide, potassium hydroxide, sodium carbonate, and potassium carbonate. This invention involves optional deprotection of the resulting compound (−)-(I) with an acid such as hydrochloric acid and trifluoroacetic acid in a solvent such as water, water-alcohol, and water-acetic acid at a temperature from 0° C. to the boiling point of the solvent in an ordinary method to give (−)-(S)-3-methylamino-4-methylenepyrrolidine of the formula:

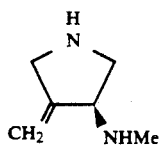

quantitatively in overall yield.

In this invention, any of known amino-protecting groups, as long as it is deprotectable without any catalytic reduction, may be used in this reaction. Those are described, for example, in "Protective Group in Organic Chemistry" edited by J. F. W. McOmie, 1973, pp. 44-74. Preferred examples of the amino-protecting groups include acyl derivatives such as benzoyl, acetyl, formyl, and trifluoroacetyl; urethane-type derivatives such as benzyloxycarbonyl, t-butoxycarbonyl, isopropoxycarbonyl, and methoxycarbonyl; and alkyl derivatives such as allyl, benzyl, trityl, and tetrahydropyranyl.

This invention will be further explained by the following examples and reference example, which are not intended to restrict the scope of this invention.

EXAMPLE 1

(−)-(S)-3-Methylamino-4-methylenepyrrolidine

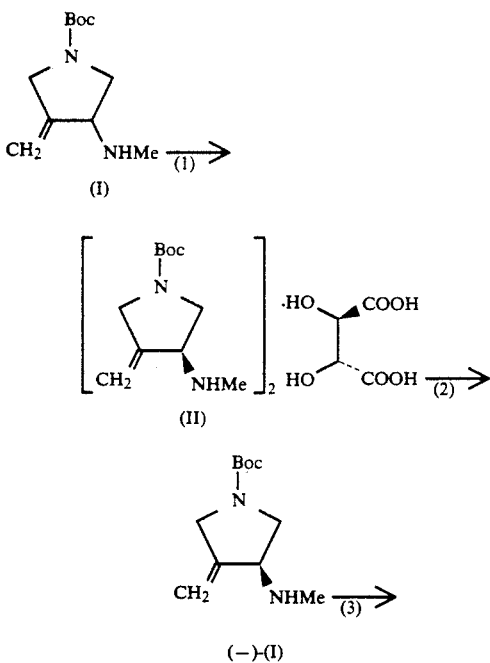

(1) A solution of 690 mg (3.25 mmol) of racemate (I) and 244 mg (1.63 mmol) of L-(+)-tartaric acid in 5 ml of methanol is evaporated to dryness. The residue is dissolved in 3.0 ml of isopropyl alcohol and the solution is allowed to stand overnight at room temperature. The reaction mixture is filtered off and the resulting precipitates are washed with a small amount of isopropyl alcohol and dried over to give 431 mg (Yield : 92%) of the compound (II) as colorless crystals.

Decomposition point : 160-162° C.,

[α]D= +10.9° (c=1.06, 24.0° C., methanol)

Anal Calcd. (%) for $C_{26}H_{46}N_4O_{10}$: C,54.34; H,8.07; N,9.75; Found : C,54.24; H,7.96; N,9.69.

NMR (CD,OD, 200M): 1.46 (s, 18H); 2.61 (s, 6H); 3.65 (d, J=15, 2H); 3.72 (d, J=15, 2H); 3.80-4.40 (m, 6H); 4.35 (s, 2H); 5.43 (s, 2H); 5.50 (s, 2H), 2p (2) A solution of 400 mg of the salt of the compound (II) in 2.0 ml of water is basified with potassium hydroxide. The reaction mixture is extracted with ether, and the ether layer is dried over $MgSO_4$. The solvent is distilled away under reduced pressure to give 271 mg (Yield : 91%) of the compound (−)-(I) as oily substance.

[α]D= −25.8° (c=1.04, 24.0° C., methanol)

(3) A solution of 24.80 g of the compound (−)-(I) obtained in (2) in 50 ml of a solution of cooled 3N-HCl-methanol is stirred at room temperature for 1.5 hours. To the reaction mixture is added ethanol, and methaol is distilled away gradually under reduced pressure. The resulting crystals are collected to give 4.0 g (Yield: 96%) of (−)-(S)-3-methylamino-4-methylenepyrrolidine.

mp.: 204°-205° C., optical purity: 100% ee

[α]D= −44.4° (c=1.10, 24.0° C., methanol) Anal Calcd. (%) for $C_6H_{12}N_2 \cdot 2HCl \cdot \frac{1}{2}H_2O$: C, 38.01; H,7.71; N,14.77; Cl,37.40; Found: C, 37.88; H,7.53; N,15.19; Cl,37.40.

NMR ($D_2O$, DDS, 200M): 2.83 (s, 3H); 3.74 (dd, J=12.5 Hz, 1H); 4.02 (dd, J=12.8 Hz, 1H); 4.17 (m, 2H); 4.60 (m, 1H); 5.76 (m, 2H).

REFERENCE EXAMPLE 1

7-((−)-(S)-3-Methylamino-4-methylenepyrrolidine)-1-cyclopropyl-6,8-difluoro-1,4-dihydro-4-oxo-3-quinolinecarboxylic acid 1

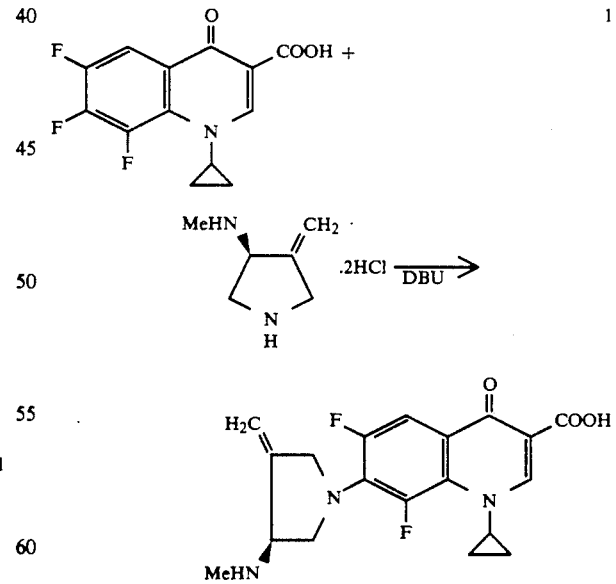

A solution of 1.33 g (4.68 mmol) of 1-cyclopropyl-6,7,8-trifluoro-1,4-dihydro-4-oxo-3-quinolinecarboxylic acid, 1.30 g (7.02 mmol) of (−)-(S)-3-methylamino-4-methylenepyrrolidine hydrochloride, and 2.70 ml of DBU in 15 ml of acetonitrile is refluxed for 2 hours. The resulting crystals are collected and recrystallized from acetonitrile to give 1.51 g (Yield: 81%) of 7-((−)-(S)-3-methylamino-4-methylenepyrrolidine)-1-cyclopropyl-6,8-difluoro-1,4-dihydro-4-oxo-3-quinolinecarboxylic acid 1. m.p. 202°-204° C. [α]D= −81.4° (c=1.01, 23.0° C., 0.1N HCl).

Anal Calcd. (%) for $C_{19}H_{19}N_3O_3F_2$: C,60.79; H,5.10; N,11.19; F,10.12; Found: C,60.49; H,5.11; N,11.43; F,10.04.

NMR ($D_2O$, 200M, 2% NaOH, DSS) 0.9-1.3 (m, 4H); 2.35 (s, 3H); 3.30-3.60 (m, 2H); 3.70-3.90 (m, 2H); 4.12 (d, J=14 Hz,1H); 4.14 (d, J=14 Hz, 1H); 5.14 (s, 1H); 5.15 (s, 1H); 7.46 (dd, J=14,2 Hz, 1H); 8.41 (s, 1H).

REFERENCE EXAMPLE 2

7-((−)-(S)-3-Methylamino-4-methylenepyrrolidine)-1-cyclopropyl-6-fluoro-1,4-dihydro-4-oxo-3-quinolinecarboxylic acid 2

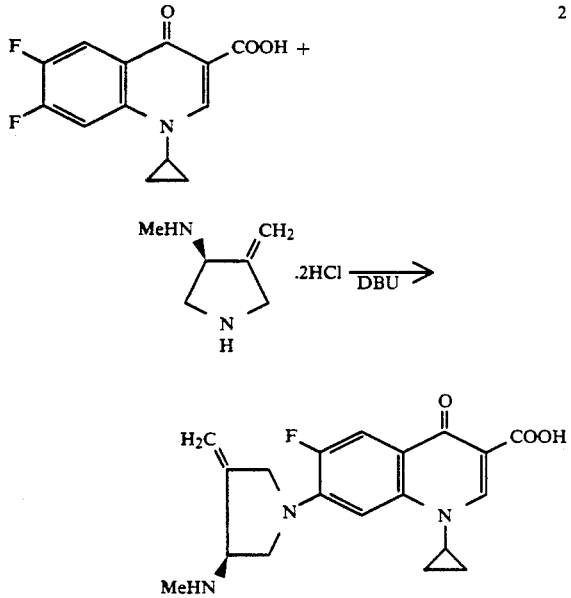

A mixture of 2.65 g (10 mmol) of 1-cyclopropyl-6,7-difluoro-1,4-dihydro-4-oxo-3-quinolinecarboxylic acid, 2.04 g (11 mmol) of (−)-(S)-3-methylamino-4-methylenepyrrolidine hydrochloride, and 4.9 ml of DBU is poured into 20 ml of acetonitrile, and the mixture is refluxed for 1 hour. The resulting crystals are collected and dissolved into dil. ammonium and the solution is evaporated under reduced pressure to distill away ammonium. The resulting crystals are collected to give 3.05 g (Yield: 85%) of the objective compound. mp. 245°-247° C.

[α]D −26.5° (C=1.01, 24.0° C., 0.1N-HCl)

Anal calcd. (%) for $C_{19}H_{20}N_3O_3F$: C,63.86; H,5.64; N,11.76; F,5.32 Found: C,63.84; H,5.92; N,11.90; F,5.45.

NMR($D_2O$, 200M, 2% NaOH, DSS). 0.7-1.3 (m, 4H); 2.32 (s, 3H); 3.0-3.3 (m, 2H); 3.4-3.6 (m, 2H); 3.7-4.0 (m, 2H); 5.13 (s, 1H); 5.14 (s, 1H); 6.43 (d, J=8 Hz, 1H); 7.42 (d, J=15 Hz, 1H); 8.30 (s, 1H).

REFERENCE EXAMPLE 3

7-((−)-(S)-3-Methylamino-4-methylenepyrrolidine)-1-cyclopropyl-8-chloro-6fluoro-1,4-dihydro-43-oxo-3-quinolinecarboxylic acid 3

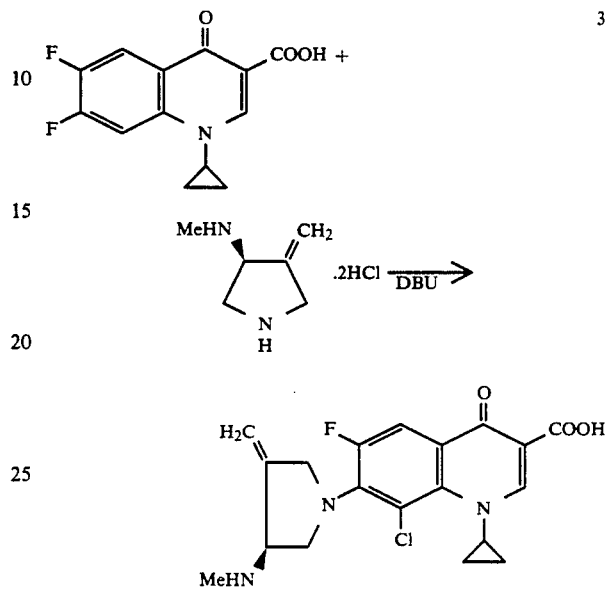

A mixture of 2.00 g (6.7 mmol) of 1-cyclopropyl-8-chloro-6-fluoro-1,4-dihydro-4-oxo-3-quinolinecarboxylic acid, 1.36 g (7.3 mmol) of (−)-(S)-3-methylamino-4-methylenepyrrolidinehydrochloride, and 3.3 ml of DBU is poured into 20 ml of acetonitrile, and the mixture is refluxed for 1.5 hours. The solution is evaporated to distill away the solvent under reduced pressure. To the residue is added ethanol, the resulting crystals are collected to give 1.38 g (Yield: 53%) of the objective compound. mp. 170°-172° C.

[α]D −13.1°(C=1.01, 24.0° C., 0.1N—HCl).

Anal Calcd. (%) for $C_{19}H_{19}N_3O_3FCl.0.2H_2O$: C,57.71; H,4.95; N,10.63; F,4.80; Cl,8.97. Found: C,57.37; H,4.93; N,10.61; F,4.97; Cl,9.50.

NMR ($D_2O$, 200M, 2% NaOH, DSS) 0.7-1.2 (m, 4H); 2.35 (s, 3H); 3.3-3.8 (m, 3H); 3.9-4.2 (m, 3H); 5.13 (s, 1H); 5.15 (s, 1H); 7.70 (d, J=14 Hz, 1H); 8.56 (s, 1H).

EXPERIMENT 1

The antibacterial activity of the compound 1, which possesses the present compound at 7-position as side chain, obtained in Reference Example 1 was determined by measuring minimum growth inhibitory concentrations in accordance with the method designated by the Japan Society of Chemotherapy. The results are shown in Table 1.

TABLE 1

| bacteria ($\times 10^6$/ml) | Minimum Inhibitory Concentration (μg/ml) | | |
|---|---|---|---|
| | (a) | (b) | (c) |
| A | 0.05 | 0.1 | 0.40 |
| B | 0.05 | 0.1 | 0.40 |
| C | 6.30 | 6.30 | 50.0 |
| D | 0.2 | 0.4 | 1.60 |
| E | 6.30 | 12.5 | 100.0 |
| F | <0.003 | 0.006 | <0.02 |

TABLE 1-continued

| bacteria | Minimum Inhibitory Concentration (μg/ml) | | |
|---|---|---|---|
| (×10⁶/ml) | (a) | (b) | (c) |
| G | 12.5 | 12.5 | 50.0 |

A *Staphylococcus aureus* SR3131
B *Staphylococcus aureus* SR3637
C *Staphylococcus aureus* SR57690FLX-R*
D *Streptococcus pneumoniae*
E *Streptococcus faecalis* SR8180FLX-R*
F *Escherichia coli* EC-7437
G *Escherichia coli* SR5038 OFLX-R*
*ofloxacin resistant bacteria
(a) Compound 1 (−)
(b) Racemate of the compound 1
(c) Ofloxacin Effect of the invention These results have clarified that the compound 1, which is optically active compound (−), shows stronger antibacterial activities than the compound racemate (±) and ofloxacin against gram-positive and -negative bacteria. Further, the present compound 1 is effective against the ofloxacin resistant bacteria.

What we claim is:

1. A process for the isolation of optically pure (−)-(S)-3-methylamino-4-methylenepyrrolidine derivatives of the formula:

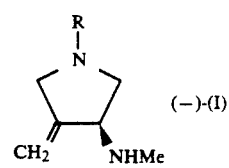

(−)-(I)

wherein R is hydrogen or amino-protecting group, from the racemic mixture of the formula (I):

(I)

wherein R has the same meaning as defined above, which comprises in a single procedure salt formation of the racemate (I) with L-(+)-tartaric acid in a molar ratio of 2:1 and subsequent treatment with a base, and optionally followed by deprotection of the amino-protecting group.

* * * * *

UNITED STATES PATENT AND TRADEMARK OFFICE
CERTIFICATE OF CORRECTION

PATENT NO. : 5,250,705
DATED : October 5, 1993
INVENTOR(S) : Tetsuo OKADA et al.

It is certified that error appears in the above-indentified patent and that said Letters Patent is hereby corrected as shown below:

Column 4, line 7, change "(CD,OD," to --($CD_3OD$--.

Column 6, line 10, change the formula to

-- 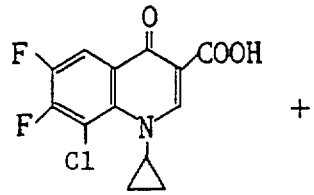    --; and line 34, change "methylenepyrrolidinehydrochloride" to --methylenepyrrolidine hydrochloride--.

Signed and Sealed this

Nineteenth Day of September, 1995

Attest:

BRUCE LEHMAN

Attesting Officer

Commissioner of Patents and Trademarks